United States Patent [19]

Buchholz

[11] 4,166,915

[45] Sep. 4, 1979

[54] PROCESS FOR THE PREPARATION OF ENDO-6-HYDROXYBICYCLO[2.2.1]HEPTANE-ENDO-2-METHANOL AND DERIVATIVES THEREOF

[75] Inventor: Fredric L. Buchholz, Midland, Mich.

[73] Assignee: The Dow Chemical Company, Midland, Mich.

[21] Appl. No.: 860,537

[22] Filed: Dec. 14, 1977

[51] Int. Cl.$^2$ .............................................. C07C 29/00
[52] U.S. Cl. ............................ 568/820; 260/343.3 R; 562/502; 568/670; 568/808
[58] Field of Search ................. 260/343.3 R; 562/502; 568/820, 808, 670

[56] References Cited

U.S. PATENT DOCUMENTS

| | | | |
|---|---|---|---|
| 2,778,838 | 1/1957 | Abe et al. | 260/343.3 R |
| 2,785,184 | 3/1957 | Sanderson | 260/343.3 R |
| 2,933,506 | 4/1960 | Ohloff | 260/343.3 R |

FOREIGN PATENT DOCUMENTS 1057108  5/1959  Fed. Rep. of Germany .... 260/343.3 R

OTHER PUBLICATIONS

Weygand et al. "Prep. Org. Chem", p. 79 (1972) John Wiley & Sons, New York.
Ramswami et al. "J. Org. Chem" 27:2761–2763 (1962).
Alder et al. "Justus Liebigs Ann der Chemies", vol. 514, pp. 197–211 (1934).

*Primary Examiner*—Norma Morgenstern
*Attorney, Agent, or Firm*—G. R. Plotecher

[57] ABSTRACT

The title compound is prepared by contacting 6-oxatricyclo[3.2.1.1$^{3,8}$]nonan-7-one with a stoichiometric amount of a reducing agent, such as lithium aluminum hydride, at reducing conditions, such as reflux temperature and pressure. This difunctional, endo-specific product is useful in the preparation of various polymer systems illustrated by polyesters, polyurethanes, polycarbonates, etc.

7 Claims, No Drawings

PROCESS FOR THE PREPARATION OF ENDO-6-HYDROXYBICYCLO[2.2.1]HEPTANE-ENDO-2-METHANOL AND DERIVATIVES THEREOF

BACKGROUND OF THE INVENTION

1. Field of the Invention

The invention relates to endo-6-hydroxybicyclo[2.2.1]heptane-endo-2-methanol, its derivatives and a process for its preparation.

2. Description of the Prior Art

The endo isomers of this invention are known compounds. However, the known processes for preparing these endo isomers are not stereo-specific and yield a mixture of endo and exo isomers. For example Brit. Pat. No. 1,011,318 teaches a process for the production of a mixture of 2- and 3-hydroxybicyclo-[2,2,1]-heptane-6-methanol by adding water to the olefinic double bond in bicyclo-[2,2,1]-heptenemethanol-(6). Fr. Pat. No. 1,434,574 teaches a process for preparing a mixture of 2-hydroxymethyl-5(6)-hydroxybicyclo-[2,2,1]-heptanes by reacting 2-hydroxymethybicyclo-[2,2,1]-heptene-(5) at a temperature between 100° C. and 180° C. and at atmospheric or superatmospheric pressure in the presence of a Lewis acid with an excess of a $C_1$–$C_4$ aliphatic monocarboxylic acid and then transesterifying the resultant diester using a monohydric aliphatic alcohol in the presence of a basic catalyst. French Addition No. 87,991 to Fr. Pat. No. 1,434,574 teaches another process for obtaining the same product mixture of Fr. Pat. No. 1,434,574, the process comprising refluxing 2-(hydroxymethyl)bicyclo[2.2.1]hept-5-ene with anhydrous acetic acid and boron trifluoride in ethyl ether for 5 hours and then heating the reaction mixture in a pressure vessel for an additional 5 hours at 150° C. Acetic acid is removed in vacuo to yield 2-(acetoxymethyl)-5(6)-acetoxybicyclo[2.2.1]heptane which is subsequently hydrolyzed to yield the mixture of hydroxy-substituted bicyclo[2.2.1]heptanes. The mixtures produced by these illustrative processes include both positional (5- and 6-hydroxy) and stereo (endo and exo) isomers. These mixtures have proven utility in the preparation of polycarbonates (Brit. Pat. No. 1,042,200) and polyurethanes (Brit. Pat. No. 1,011,318).

SUMMARY OF THE INVENTION

According to this invention, endo-6-hydroxybicyclo[2.2.1]heptane-endo-2-methanol or a derivative thereof, is selectively prepared by contacting 6-oxatricyclo[3.3.1.1$^{3,8}$]nonan-7-one or a derivative thereof with a stoichiometric amount of a reducing agent of sufficient reducing power to reduce the nonan-7-one to the methanol at reducing conditions. This process is not only stereo-specific for the endo-isomer but it is also characterized by exceptionally high (in excess of 95 percent) yields. Moreover, this process is an integral step in the synthesis of useful, difunctional products from cyclopenta-1,3-diene.

DETAILED DESCRIPTION OF THE INVENTION

The 6-oxatricyclo[3.2.1.1$^{3,8}$]nonan-7-one here used is of the formula

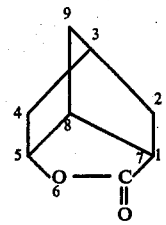

(I)

Derivatives of I can have a wide variety of substituents at various positions on the bridged carbocycle. The substituents are generally inert, i.e., nonreactive with either the process reagents or products at the process conditions, and include such moieties as halogen, aryl, $C_1$–$C_5$ alkyl, alkoxy, hydroxyl, hydroxyalkyl, etc. The derivatives of I here used generally have a total carbon content, excluding the bridged carbocycle, of 10 carbon atoms and preferably of about 5 carbon atoms. "Bridged carbocycle" means the carbocycle ring in I defined by positions 1–5 and 8–9. Although the substituents can be located at any position upon this carbocycle, they are most often located at the 2, 4 and 9 positions. For reasons of convenience, 6-oxatricyclo[3.2.1.1$_{3,8}$]nonan-7-one is the preferred starting material.

The oxatricyclo[3.2.1.1$^{3,8}$]nonan-7-ones of this invention can be readily prepared by any one of a number of conventional methods, such as by slowly contacting with continuous stirring the corresponding bicyclo[2.2.1]hept-5-ene-2-carboxylic acid (II) with a strong protic acid, e.g., sulfuric acid.

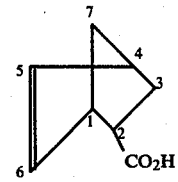

(II)

The carboxylic acids can also be readily prepared by any one of a number of conventional methods, such as by contacting the corresponding cyclopenta-1,3-diene with an appropriate $\alpha,\beta$-unsaturated carboxylic acid, e.g., acrylic acid.

Any reducing agent of sufficient reducing power to reduce I to the hydroxyl-substituted bicyclo[2.2.1]heptane methanol (III) can be here used.

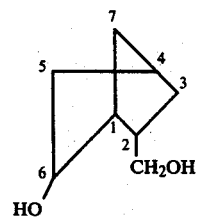

(III)

Lithium aluminum hydride is illustrative but other reducing agents include sodium aluminum hydride, diborane, sodium metal in an alcohol (such as a $C_1$–$C_6$ aliphatic alcohol, a glycol, etc.), hydrogen gas in combination with a reducing catalyst (such as copper-chromium oxide, nickel-chromium oxide, etc.), and the like. Although a stoichiometric amount of the reducing agent is required for the practice of this invention, excess amounts can be employed where convenient (e.g., pressurizing with hydrogen a closed reaction vessel containing I and a copper-chromium oxide catalyst).

The reducing agent and I are contacted at reducing conditions, i.e., conditions at which the reducing agent can reduce I to III. The reducing conditions are, of course, defined by the reducing agent. For example, the reducing conditions wherein lithium aluminum hydride is the reducing agent are typically the reflux temperature of the reaction mixture (I, reducing agent and solvent) and atmospheric pressure. If hydrogen in combination with a reducing catalyst is used, then reducing conditions of about 100° C.–200° C. and a hydrogen pressure between about 200 and 300 atmospheres are generally employed. Sodium metal and alcohol generally require conditions sufficient to cause the alcohol to boil while diborane is effective at ambient temperature and atmospheric pressure.

The reagents, i.e., I and the reducing agent, are generally solubilized in a suitable, inert (as previously defined) liquid solvent. Polar solvents are preferred over nonpolar solvents and illustrative polar solvents include tetrahydrofuran, glyme, diethyl ether, ethanol and the like.

Endo-6-hydroxybicyclo[2.2.1]heptane-endo-2-methanol (III) is a white, crystalline solid when recrystallized from mixed hexanes. This material has a melting point between about 107° C. and 110° C. and a boiling point at about 0.1 torr. of about 120° C. Of course, the substituents, if any, of III will correspond to the substituents, if any, of I.

The following examples are illustrative of certain embodiments of this invention. Unless otherwise indicated, all parts and percentages are by weight.

SPECIFIC EMBODIMENTS

EXAMPLE 1

Preparation of Bicyclo[2.2.1]hept-5-ene-2-carboxylic Acid

Freshly distilled cyclopenta-1,3-diene (66.11 g) was added to a solution of freshly distilled acrylic acid (73 g, inhibited with p-methoxyphenol) and diethyl ether (75 ml). The solution had a temperature between 5° C. and 10° C. The exothermic reaction that ensued was controlled by an ice bath. The cyclopentadiene was added to the solution over a period of 30 minutes and after all the cyclopentadiene had been added, the solution was allowed to warm to ambient temperature. After a reaction period of 4 hours, gas chromatographic (GC) analysis indicated a yield of 100 percent of theory of the carboxylic acid. The carboxylic acid was recovered from the diethyl ether by vacuum distillation.

EXAMPLE 2

Preparation of 6-Oxatricyclo [3.2.1.1$^{3,8}$]-nonan-7-one

The carboxylic acid (51 g) prepared in Example 1 was slowly added with stirring to sulfuric acid (500 ml, 75 percent by volume). The exothermic reaction that ensued was controlled by an ice-water bath. The reaction subsided after several minutes and the resulting dark solution was then kept at room temperature for about 10 days. The solution was then poured into ice-water (150 ml) and the product then extracted with diethyl ether (three 200-ml portions). The combined extracts were washed with saturated sodium bicarbonate solution (200 ml). The ether was evaporated yielding 45.5 g of 6-oxatricyclo[3.2.1.1$^{3,8}$]nonan-7-one which was about 91 percent of theory. The product was identified by GC-mass spectrometric, infrared and melting point analysis.

EXAMPLE 3

Preparation of Endo-6-hydroxybicyclo[2.2.1]heptane-endo-2-methanol

A 250 ml, 3-necked reaction flask equipped with an addition funnel, reflux condenser with drying tube and magnetic stirrer was charged with dry tetrahydrofuran (50 ml) and lithium aluminum hydride (4 g) and subsequently stirred under reflux for 1 hour. The nonan-7-one (10 g) prepared in Example 2 was dissolved in tetrahydrofuran (50 ml) and then slowly added over a 10-minute interval to the hydride solution. After the addition of all the nonan-7-one, refluxing was continued for an additional 2 hours. The excess hydride was carefully decomposed by the slow addition of water and the concurrent reduction of the reaction temperature to ambient. The solid salts were separated by filtration through a glass filter, then washed with two 50-ml volumes of fresh tetrahydrofuran. The tetrahydrofuran was then removed to yield endo-6-hydroxybicyclo[2.2.1]heptane-endo-2-methanol (95 percent of theory). The product was confirmed by GC-mass spectrometric and nuclear magnetic resonance analysis.

The overall yield of the methanol based upon cyclopenta-1,3-diene was in excess of 86 percent. Hence, the process of this invention generates a useful difunctional product from cyclopentadiene.

Although the invention has been described in considerable detail through the preparation of endo-6-hydroxybicyclo[2.2.1]heptane-endo-2-methanol, such detail was for the purpose of illustration only and many variations and modifications can be made by one skilled in the art without departing from the spirit and scope of this invention.

What is claimed is:

1. A stereo-specific process for preparing endo-6-hydroxybicyclo[2.2.1]heptane-endo-2-methanol or a derivative thereof, the process comprising contacting at reducing conditions 6-oxatricyclo[3.2.1.1$^{3,8}$]nonan-7-one or a derivative thereof with at least a stoichiometric amount of a reducing agent of sufficient reducing power to reduce the nonan-7-one to the methanol.

2. The process of claim 1 wherein the reducing agent is selected from the group consisting of lithium or sodium aluminum hydride, diborane, sodium metal in an alcohol, and hydrogen in combination with a reducing catalyst.

3. The process of claim 1 wherein the reducing agent is lithium aluminum hydride.

4. The process of claim 3 wherein the nonan-7-one or derivative thereof and the hydride are dissolved in an inert, liquid solvent.

5. The process of claim 4 wherein the solvent is tetrahydrofuran.

6. The process of claim 5 wherein the contacting is conducted at reflux temperature and atmospheric pressure.

7. A process for preparing endo-6-hydroxybicyclo]2.2.1]heptane-endo-2-methanol and derivatives thereof from cyclopenta-1,3-diene, the process comprising:
   (1) preparing bicyclo]2.2.1]hept-5-ene-2 carboxylic acid or a derivative thereof from cyclopenta-1,3-diene and an α,β-unsaturated carboxylic acid;
   (2) preparing 6-oxatricyclo[3.2.1.1$^{3,8}$]-nonan-7-one or a derivative thereof from the bicyclo ]2.2.1]hept-5-ene carboxylic acid or derivative thereof; and
   (3) preparing the methanol from the nonan-7-one by the process defined in claim 1.

* * * * *